United States Patent [19]

Reisberg et al.

[11] 4,385,053

[45] May 24, 1983

[54] TREATMENT FOR HUMAN MEMORY IMPAIRMENT ASSOCIATED WITH AGING

[76] Inventors: Barry Reisberg, 20 Waterside Plz. #7K, New York, N.Y. 10010; Steven H. Ferris, 33 Marie Dr., Huntington, N.Y. 11743

[21] Appl. No.: 242,750

[22] Filed: Mar. 11, 1981

[51] Int. Cl.³ .................... A61K 31/40; A61K 31/685
[52] U.S. Cl. .................................... 424/199; 424/274
[58] Field of Search ............................. 424/274, 199

[56] References Cited

PUBLICATIONS

Interdisciplinary Topics in Gerontology, Pub. S. Karger, Basel 1979, Chpt. *Pyschopharmacologic Aspects of Cognitive Research in the Elderly: Some Current Perspectives*, p. 132–152, Reisberg et al.
Lavat, Oct. 1, 1977 p. 711.

*Primary Examiner*—Stanley J. Friedman
*Attorney, Agent, or Firm*—Gottlieb, Rackman & Reisman

[57] ABSTRACT

A process is disclosed for treating human memory impairment associated with aging, such as occurs in Alzheimer's disease, by administering a central nervous system cholinergic precursor such as lecithin or a choline salt in construction with a metabolic enhancer such as piracetam.

5 Claims, No Drawings

TREATMENT FOR HUMAN MEMORY IMPAIRMENT ASSOCIATED WITH AGING

BACKGROUND OF THE INVENTION

The present invention relates to a new and useful process for the treatment of human cognitive disorders by administering a metabolic enhancer such as piracetam in combination with a cholinergic precursor such as lecithin.

It has been estimated that at least 10% of persons over the age of 60 will eventually suffer severe mental deterioration. A much larger number will experience sufficient cognitive decline to impede their activities. At the other end of the spectrum, more than half of the residents in nursing homes in the United States have been classified as senile. Prior to the present invention, it has been generally concluded that there is no currently available treatment for age-related cognitive deterioration. Apparently the lack of an effective treatment is due to a lack of understanding of the underlying etiology of cognitive decline. Reisberg, B.; Ferris, S. and Gershon, S. "Psychopharmacological Aspects of Cognitive Research in the Elderly: Some current perspectives." In: INTERDISCIPLINARY TOPICS OR GERONTOLOGY, W. Meir-Ruge and H. von Hahn (eds.), S. Karger, Basel 15:132-152, 1979 (copy enclosed). In particular, several current treatments based upon the hypothesis of cerebral arteriosclerotic etiology had not been shown to be of any value. Reisberg et al., op. cit., p. 133. Examples of these unsuccessful attempts are treatment with cerebral vasodilators to increase blood flow and treatment with hyperbaric oxygen to increase cerebral oxygen supply. Treatments with psychoactive drugs for the modification of behavioral symptoms have had no effect upon cognitive performance.

Substances related to the present invention have been considered individually in connection with human senility but heretofore not been demonstrated to act synergistically in combination upon humans in a positive clinically significant manner.

U.S. Pat. No. 3,459,738 disclosed the synthesis of the compound 2-oxy-pyrrolidone acetamine (piracetam) for its marked effect upon the involuntary rythmical oscillation of the eyeballs known as nystagmus. It is a nootropic derivative of gamma-aminobutyric acid capable of crossing the blood-brain barrier.

The effects of piracetam on both human and animal subjects has been studied. In elderly patients, piracetam has had no significant positive effect on the cognitive state of those severely impaired by senile dementia (e.g., those who had to be accompanied for out-patient treatment or who were unable to function is society) (Reisberg, op cit., 137-138). On elderly patients with mild or moderate cognitive decline piracetam has had some positive effect in short term therapeutic trials (up to twelve weeks), although not proved to be of definite value in reversing or even slowing the progressive memory or other cognitive deficit which sometimes occurs with aging. See, e.g., Stegink, A. J., "The clinical use of Piracetam, a new nootropic drug: The treatment of symptoms of senile involution", *Argn. Forsch* (Drug Research), 22/6:975-977, 1972; Stegink, A. J. and Tjeerdsma, H., "Piracetam: Controlled study in a group of patients with cerebral arteriosclerosis", DE73G181. UCB-Pharmaceutical Division, DRDM-Clinical Development, Brussels, Belgium.

There has been some very recent work indicating that piracetam does improve visual memory in patients with mild to moderate senile dementia, Alzheimer's type (SDAT). Again, this work does not indicate an effectiveness for piracetam that is suitable for clinical treatment. (Branconnier, R. J., and Cole, J. O., "Final report of a clinical trail of the efficacy and safety of piracetam in the amelioration of the neuropsychological symptoms associated with mild primary degenerative dementia", unpublished manuscript, dated Apr. 22, 1980.).

The primary effectiveness noted for piracetam, aside from its effect upon nystagmus has been in treating persons of various ages for the symptoms of alcohol withdrawal, sickle cell anaemia, vertigo and in improving recovery after brain surgery.

U.S. Pat. No. 4,221,784 disclosed the process of administering lecithin to increase acetylcholine levels in the brain to alleviate the effects of tardive dykinesia, manic-depressive disease, memory impairment or familial ataxis. This disclosure was based on only one example involving just one patient who had suffered memory loss and whose memory quotient by the Wechsler Memory and Intelligence test increased from 122 to 140 after 6 weeks of lecithin ingestion. This result does not claim nor suggest may clinical effectiveness of lecithin for the treatment of senile dementia.

The interest of the present inventors in acetylcholine levels derives from the hypothesis that memory function may be related to interneuronal synaptic events and activities. One of the major known neurotransmitter systems of the brain believed to play a role in age-associated cognitive decline is the cholinergic, which is affected by acetylcholine. The cholinergic system of the brain has been shown to be strongly related to memory functioning. However, any simple direct connection between reducing memory impairment and increasing acetylcholine levels in moderately impaired outpatients has not been demonstrated. For example, deanol, which presumed to increase brain acetylcholine was given in a 4-week open trail to 14 such patients and produced no changes in memory. Ferris, S. H., Sathananthan, G., Gershon, S. and Clark, C. "Senile dementia. Treatment with Deanol." *J. Am. Geriat. Soc.*, 25:241-44 (1977). Similarly, an open, dose-ranging study using up to 20 g/day of choline chloride, a cholinergic precursor and direct cholinergic agonist, gave no consistent improvement in cognitive test performance. Ferris, S. H.; Sathananthan, G.; Reisberg, B. and Gershon, S. "Long Term Choline Treatment of Memory Impaired Elderly Patients", *Science* 205, 1039-40, 1979.

In summary, although both a choline/lecithin treatment or a piracetam treatment may produce some small cognitive effects in senile dementia patients, neither therapy is of clinically significant value, at least with treatment durations of up to three months.

Choline and piracetam has been administered in combination to rats. This improved the rats' performance in one-trail passive avoidance procedure over their performance when receiving only choline or piracetam. Bartus, R. T., "Pharmacological manipulations of age-related neurobehavioral dysfunctions." Paper presented at the 10th Annual National Meeting of the American Aging Association, Oct. 2-4, 1980, Houston, Texas.

Prior to the present invention autopsy studies on humans lead to reclassification of senile dementia into "Senile dementia, Alzheimer's type (SDAT)", or "multi-infarct dementia (MID)", or senile dementia secondary to mixed causes, including both SDAT and MID. SDAT is now thought to account for more than 50% of all cases of senile dementia. Alzheimer's disease (i.e., SDAT) is only know to occur in humans, thereby limiting the significance of etiological analogies from animal studies.

Alzheimer's disease is defined neuropathologically as the presence of neurofibrillary tangles (NFT's) together with senile plaques. The NFT's of the Alzheimer's type are only known to occur in human beings, furthermore, the association of NFT's with senile plaques is a uniquely human phenomenon. Hence, Alzheimer's disease is only known to occur in human beings, thereby limiting the significance of animal analogies. Thus, prior to the present invention, it was not known that the major cause of human senile dementia would respond with clinically significant positive results to the process of the present invention or that the combination of clinically insufficient therapies would co-act synergistically in human patients to provide a significant clinical therapy.

SUMMARY OF THE INVENTION

This invention is based upon the discovery that a metabolic enhancer such as piracetam in combination with a central nervous system cholinergic precursor such as dietary or nutritional choline or lecithin is clinically effective in humans for treatment of the cognitive and behavioral symptoms of SDAT to an extent greatly in excess of the benefits of either type substance administered individually. The combination is effective if orally administered.

One of the objects of the present invention is to provide a clinically effective treatment for Alzheimer's disease, senile dementia and memory impairment associated with aging. A further object of the present invention is to provide a clinically effective treatment to enhance the limited efficacy of piracetam in the treatment of Alzheimer's disease. A still further object of the present invention is to provide a treatment wherein the administration of a metabolic enhancer potentiates the ability of a cholinergic precursor to improve the functional activity of the cholinergic system in humans.

DETAILED DESCRIPTION OF A PREFERRED EMBODIMENT

In accordance with this invention, elderly patients with cognitive impairment are treated by the oral administration of lecithin and piracetam or choline and piracetam. Lecithin is preferably orally administered in amounts of 0.1-200 g/day, usually 10-100 g/day. Alternatively, the lecithin is administered in usual dosages of between about 2 and 25 gms. of phosphotidyl choline content per day. Choline is preferably administered orally as a salt, e.g., choline chloride. The dose of the latter is 1 g to 30 g/day, usually 3 to 16 g/day. Piracetam is preferably administered orally in a dose of 800 mg. to 20 g daily, usually 2.4-7.2 g daily. The treatment is effective within about one week.

The following example illustrates the effect of a preferred embodiment of the invention:

Fifteen elderly outpatients (60-85 years of age) with mild to moderate cognitive impairment received 9 g choline chloride and 4.8 g piracetam daily for a period of only one week. Mean scores before and after treatment on the Buschke Selective Reminding Task, which measured verbal learning and memory, are given in Table 1. Separate mean scores for memory storage and memory retrieval are given for each of five learning trails, as well as for delayed recall (30 min. later). As seen from these results, there was a consistent pattern of improvement with treatment (1 week vs. baseline).

TABLE 1

MEAN BUSCHKE TEST SCORES OF 15 MILDLY TO MODERATELY IMPAIRED ELDERLY OUTPATIENTS BEFORE AND AFTER 1-WEEK TREATMENT.

| Trial # | Storage | | Retrieval | |
|---|---|---|---|---|
| | Baseline | 1 Week | Baseline | 1 Week |
| Trial 1 | 4.93 (2.93)* | 5.73 (4.93) | 4.93 (2.93) | 5.73 (2.63) |
| Trial 2 | 7.26 (2.93) | 7.80 (2.30) | 6.00 (3.02) | 6.13 (2.79) |
| Trial 3 | 8.06 (2.93) | 8.33 (3.95) | 5.66 (3.03) | 6.73 (2.34) |
| Trial 4 | 8.73 (2.18) | 9.06 (1.43) | 6.33 (2.81) | 6.66 (2.66) |
| Trial 5 | 8.86 (2.03) | 9.26 (1.38) | 6.40 (2.66) | 6.66 (3.77) |
| Delayed | 8.06 (3.43) | 9.13 (1.40) | 5.00 (3.64) | 5.93 (2.68) |

*Standard deviations (SD's) are given in parentheses.

The data of Table 1 represents the average number of words recalled correctly. A perfect score is 10.0. "Storage" refers to the cumulative recall of the patient over several trails and is a measure of the number of different words out of 10 which the patient was able to enter into the storage component of his memory. "Retrieval" refers to the number of stored words that were recalled on a particular trail.

The Buschke verbal learning task is a verbal learning procedure in which lists of ten words are learned using the method of "selective reminding". Buschke, H., and Fuld, P. A.: "Evaluating storage, retention, and retrieval in disordered memory and learning", Neurology, 11:1019-1025 (1974).

Previous studies with choline chloride alone (Ferris, S. H., Sathananthan, G., Reisberg, B., and Gershon, S., "Long-term choline treatment of memory impaired elderly patients", Science, 205:4410 pp. 1039-1040, 1979) or piracetam alone (Reisberg, B., Ferris, S. H., Corwin, J., McCarthy, M. and Schneck, M., "Effects of Piracetam in the Cognitively Impaired Aged", Journal of the American Aging Assocs. 3:4, 113 1980 (abstract)) have failed to show such consistent effects and these results are contrasted below.

The beneficial effects of the present invention on particular patients were highlighted by the following further analysis. The study psychiatrist, who did not have access to the test scores, rated four patients in the group as significantly improved clinically, based upon psychiatric interviews. The test scores for these patients were examined separately; each subject showed marked improvement, as summarized in Table 2. Such dramatic and clinically significant improvement in 27% of the subjects has not previously been observed with choline/lecithin or piracetam alone. These results imply a synergistic effect for at least some subjects.

TABLE 2

MEAN BUSCHKE TEST SCORES OF 4 PATIENTS SHOWING CLINICAL RESPONSE TO 1-WEEK TREATMENT

| Trial # | Storage | | | Retrieval | | |
|---|---|---|---|---|---|---|
| | Base-line | 1 Week | % Change | Base-line | 1 Week | % Change |
| Trial 1 | 2.25 (1.71)* | 4.50 (1.73) | 100.0 | 2.25 (1.71) | 4.50 (1.73) | 100.0 |
| Trial 2 | 4.50 (3.32) | 6.25 (3.30) | 38.9 | 3.75 (3.00) | 4.25 (0.96) | 13.3 |
| Trial 3 | 5.50 (4.20) | 8.00 (2.71) | 45.5 | 3.50 (2.39) | 5.75 (1.50) | 64.3 |

TABLE 2-continued

MEAN BUSCHKE TEST SCORES OF 4 PATIENTS SHOWING CLINICAL RESPONSE TO 1-WEEK TREATMENT

| Trial # | Storage | | | Retrieval | | |
|---|---|---|---|---|---|---|
| | Base-line | 1 Week | % Change | Base-line | 1 Week | % Change |
| Trial 4 | 7.25 (2.98) | 8.25 (2.22) | 13.8 | 4.25 (1.26) | 7.25 (1.71) | 70.6 |
| Trial 5 | 7.25 (2.99) | 8.25 (2.22) | 13.8 | 4.25 (1.50) | 4.50 (3.00) | 5.9 |
| Delayed | 6.50 (4.44) | 8.25 (2.22) | 26.9 | 2.75 (2.75) | 4.75 (1.26) | 72.7 |

*SD's are in parentheses.

These results may be contrasted with a study of the effects of the drugs individually. Slightly higher dosages of piracetam and choline chloride were administered individually in two separate tests of their individual efficacy. The piracetam study covered a 10-week period with four weeks of active treatment and six weeks of placebo administration, and comprised sixteen elderly patients 60 to 85 years of age with presumptive diagnoses of benign senescent forgetfulness or senile dementia of the Alzheimer's type. There was some minimal improvement of memory but not of present clinical significance. Of twenty psychometric measures, two relating to memory showed effects favoring piracetam. Memory improved on a First and Last Names task measuring verbal associative memory and on a delayed facial recognition task.

The choline chloride study covered a 16-week period with six weeks of active treatment and ten weeks of placebo administration, and comprised 45 patients 60–85 years of age who also suffered from mild to moderate cognitive impairment. Globally, there were no clinically significant treatment effects with choline chloride. For over half the subjects there was no difference, globally, between choline chloride and placebo.

However, there were some statistically significant changes on a few of the many cognitive tests, although not of clinical impact. Several measures showed an improvement in recent memory, with little or no changes in psychomotor performance or other non-memory measures.

Buschke tests were also administered in the separate piracetam and choline studies, but did not exhibit clinically significant positive results.

The inventors believe that the following explanation of the efficacy of the invention is correct. There is strong evidence that the memory deficits of SDAT are related directly to the loss or dysfunction of cholinergic neurons. First of all, a series of recent postmortem neuropathological studies of Alzheimer's patients have revealed a selective loss of cholinergic neurons. Secondly, in SDAT there is a dramatic reduction in choline acetyltransferase (CAT) activity. CAT is the enzyme responsible for the synthesis of acetylcholine from choline. The marked reduction in CAT occurs only in SDAT, with only minimal reductions is age-matched normals or MID. Furthermore, the loss of CAT has been shown to occur in vivo, based upon brain biopsy data, and the magnitude of reduction in CAT is apparently correlated with the degree of cognitive impairment prior to death.

The inventors believe there is a metabolic explanation for the utility of the piracetam in combination with a cholinergic precursor to reverse this cholinergic insufficiency. Conditions which interfere with cerebral metabolism and which impair cerebral carbohydrate oxidation, have been shown to cause a decrease in acetylcholine synthesis proportional to the reduction in oxidation. Gibson, G. E., Blass, J. P., and Jenden, D. M., "Measurement of acetylcholine turnover with glucose used as a precursor: Evidence for compartmentation of glucose metabolism in brain", *J. Neurochem.*, 30:71, 1978.

Hence, the observed deficits in the synthesis and release of acetylcholine in SDAT may be secondary to a pre-existing metabolic deficiency accompanying the disorder. Recent studies performed in our laboratories strongly support this hypothesis of a pre-existing metabolic deficiency. Using a recently developed technique known as positron emission tomography, Ferris, et al., Neurobiology of Aging, Experimental and Clinical Research, 1:127–131, 1980, have found a large statistically significant diminution in the rate of glucose utilization in patients with senile dementia of the Alzheimer's type. Furthermore, the degree of diminution in metabolic activity in SDAT was highly correlated with objective measures of degree of cognitive impairment.

Accordingly, the combination treatment with a substance such as piracetam, which remediates the metabolic deficiency, (e.g., enhanced ATP/ADP ratio, improved electrophysiologic functioning), with one which enhances cerebral cholinergic functioning, results in a dramatically effective reversal of the disease process, even over the course of only one to several weeks.

The possibility that the combined effects of both treatments may be much more than additive has now been verified clinically for humans.

A further explanation for the remarkable efficacy of the present invention came from evidence that piracetam increases the incorporation of $^{32}p$ into phosphotidylcholine (lecithin) in neurons and glial cells isolated from rabbit cerebral cortex. Woelk, H.: "Effects of piracetam on the incorporation of $^{32}p$ into the phospholipids of neurons and glial cells isolated from rabbit cerebral cortex", *Pharmakopsychiat.*, 12:251–256 (1979). This result implies that piracetam increases the rate of turnover of choline and this is apparently related to cholinergic neurotransmission; so that the combination of a central acetylcholine precursor (such as choline chloride or lecithin), with piracetam, produces a synergistic effect on learning paradigms. This is consistent with the observation that a cholinergic precursor alone, such as lecithin, will have little effect upon remediation of a central cholinergic deficiency, since "flooding" the presynaptic region with choline salt will only slightly increase its post-synaptic neurotransmitter properties. Similarly, increasing post-synaptic membrane phosphotidyl choline turnover with piracetam may improve cholinergic neurotransmission; however, this effect would be expected to be small in the absence of increased central acetylcholine precursor availability (e.g., with choline chloride or lecithin).

Thus, there is now an understanding of the underlying etiology of cognitive decline consistent with the unexpected synergistic effect of the present enhancer and cholinergic precursor. This is the first serious candidate for therapy to reverse the deficit in SDAT.

Medications believed to be effective as metabolic enhancers other than piracetam are dihydroergotoxin, vincamine, naftidrofuryl, papaverine, isoxsuprine, cyclandelate and centrophenoxine (Reisberg, B, "Metabolic Enhancers and Agents Effecting Blood Flow and Oxygen Utilization", in *Strategies for the Development of an Effective Treatment for Senile Dementia*, T. Crook and S. Gershon (Eds.), Mark Powley Associates, in press.

This invention is also believed to be effective for the treatment of human patients suffering from memory impairment secondary to a decrease in brain acetylcholine availability. Entities in which said causes of memory impairment are likely include the memory impairments of patients with Parkinsonism, Huntington's chorea, tardive dyskinesia, chronic schizophrenia, anxiety states, multi-infarct dementia, affective disorder, and Gilles de la Tourette syndrome.

We claim:

1. The process of treating a human patient suffering from memory impairment associated with aging comprising administering for a period of time in excess of about 7 days a combination of medications comprising the central nervous system cholinergic precursor lecithin and the metabolic enhancer piracetam, wherein said piracetam is administered orally in dosages of between about 800 mg and 20 grams per day and said lecithin is administered in dosages of between 2 and 25 grams of phosphatidyl choline content per day.

2. The process of treating a human patient suffering from memory impairment associated with aging comprising administering for a period of time in excess of about 7 days a combination of medications comprising a salt of choline that is a central nervous system cholinergic precursor administered in dosages of between about 1 gram to 30 grams per day and piracetam administered in dosages between about 800 mg and 20 grams per day.

3. The process of claim 2 wherein said salt of choline is choline chloride.

4. The process of treating a human patient suffering from memory impairment associated with aging comprising administering for a period of time a combination of medications comprising the central nervous system cholinergic precursor choline chloride administered in dosages between about 3 grams to 16 grams per day and piracetam administered orally in dosages between about 2.4 grams and 20 grams per day.

5. The process of treating a human patient suffering from memory impairment associated with aging comprising administering for a period of time a combination of medications comprising the central nervous system cholinergic precursor lecithin administered in dosages of between about 0.1 gram and 20 grams per day and piracetam administered orally in dosages of between about 800 mg and 20 grams per day.

* * * * *